United States Patent [19]

Lenz et al.

[11] 4,024,173

[45] May 17, 1977

[54] PROCESS FOR THE MANUFACTURE OF CYCLOHEXENE DICARBOXYLIC ACID ESTERS

[75] Inventors: Arnold Lenz, Cologne-Stammheim; Otto Bleh, Bergheim, Sieg; Harald von Metnitz, Ranzel, all of Germany

[73] Assignee: Dynamit Nobel Aktiengesellschaft, Troisdorf, Germany

[22] Filed: Dec. 10, 1974

[21] Appl. No.: 531,419

Related U.S. Application Data

[63] Continuation of Ser. No. 161,339, July 9, 1971, abandoned, which is a continuation-in-part of Ser. No. 160,061, July 6, 1971, abandoned, which is a continuation of Ser. No. 757,103, Sept. 3, 1968, abandoned.

[30] Foreign Application Priority Data

Sept. 2, 1967 Germany .............................. 54002

[52] U.S. Cl. .......................................... 260/468 K
[51] Int. Cl.$^2$ ........................................ C07C 67/30
[58] Field of Search ................................ 260/468 K

[56] References Cited

FOREIGN PATENTS OR APPLICATIONS 1,577,846   6/1969   France ............................... 260/468

*Primary Examiner*—Robert Gerstl
*Attorney, Agent, or Firm*—Burgess, Dinklage & Sprung

[57] ABSTRACT

The hydrogenation of benzene dicarboxylic acid mono and diesters to corresponding cyclohexene dicarboxylic acid mono and diesters by carrying out the hydrogenation in the active and effective presence of alkalimetal amalgam and an alcohol in a substantially anhydrous environment. The hydrogenation reaction medium should be a mixture of the above referred to alcohol and an aromatic hydrocarbon such as toluene.

13 Claims, No Drawings

PROCESS FOR THE MANUFACTURE OF CYCLOHEXENE DICARBOXYLIC ACID ESTERS

This is a continuation, of application Ser. No. 161,339, filed July 9, 1971 which in turn is a continuation-in-part of Ser. No. 160,061 of July 6, 1971 which in turn is a continuation of Ser. No. 757,103 of Sept. 3, 1968, all now abandoned.

The invention relates to a process for the manufacture of cyclohexenedicarboxylic acid esters by the hydrogenation of benezenedicarboxylic acid esters with alkali amalgam.

It is known that by hydrogenating benzenecarboxylic acids with hydrogen in the presence of Raney nickel or platinum, a complete hydrogenation of the benzene nucleus is achieved, thereby producing derivatives of cyclohexane.

It is furthermore known that the hydrogenation of the sodium salts of benzenedicarboxylic acids in an aqueous alkaline solution with sodium amalgam results in products that are partially hydrogenated in the nucleus ("Berichte der deutschen Chemischen Gesellshaft" 61 (1928), 5, pp. 871 to 883). This method, however, has the disadvantages that, in addition to the fact that it produces a mixture of ditetra- and hexahydrogenated benzenecarboxylic acids, the carboxyl groups are hydrogenated to hydroxymethyl groups and even to methyl groups.

In another known process, terephthalic acid dimethyl ester is said to be hydrogenated with alcohol and sodium amalgam to hydroxymethyl benzoic acid (Japanese patent application No. 8 343/66).

It is the object of the invention to make available a process for the manufacture of cyclohexenedicarboxylic acid esters.

Other and additional objects of this invention will become apparent from a consideration of this entire specification including the claims hereof.

In accord with and fulfilling these objects, one aspect of this invention resides in a process of hydrogenating benzene dicarboxylic acid esters to their corresponding cyclohexane dicarboxylic acid ester derivatives by carrying out the hydrogenation in the liquid phase with an alkali metal amalgam in an anhydrous system in the presence of an alcohol and an aromatic hydrocarbon. The following are preferred embodiments of this invention directed first to the hydrogenation of benzene dicarboxylic acid methyl esters and next to the hydrogenation of benzene dicarboxylic acid esters having more than one carbon atom in the esterifying alcoholic moiety.

a. The hydrogenation of benzenedicarboxylic acid methyl esters, which may be only partially esterified if desired, is performed with alkali metal amalgam and alcohol in the presence of aromatic hydrocarbons. Surprisingly, it has been found that the aromatic hydrocarbon exercises a catalytic influence, so that, for example, in the hydrogenation of terephthalic acid dimethyl ester, a cyclohexenedicarboxydimethyl ester is produced, which is substantially uniformly tetrahydrogenated in the benzene nucleus and has a substantially uniform position isomerism.

b. The hydrogenation of benzene polycarboxylic acid esters containing ester groups having more than one carbon atom, preferably up to 18 carbon atoms, and especially up to 10 carbon atoms, is performed with alkali metal amalgam and with a primary alcohol containing 1 to 18, and especially 1 to 10 carbon atoms, or with secondary or tertiary alcohols.

The procedure described above under (a) is especially suitably for hydrogenation, by means of alkali metal amalgam and methanol, of benzenedicarboxylic acid methyl esters, which, if desired, are only partially esterified, because in this hydrogenation the desired end product is obtained in the desired manner only if at least one catalytically acting aromatic hydrocarbon such as toluene is present. The presence of aromatic hydrocarbons, which is required in the above-described methyl ester case, nevertheless offers advantages even when operating by the procedure b described above, although the presence of aromatic hydrocarbons is not essential in that procedure.

The benzene dicarboxylic acid esters are terephthalic acid mono and diesters, isophthalic mono and diesters and the mono and diesters of phthalic acid. It is preferable to use, as the aromatic hydrocarbons, benzene or alkylated hydrocarbons, especially toluene or xylene.

It is desirable to use, as the hydrogen donor for the hydrogenation of the benzene nucleus, an alcohol that corresponds to the alcoholic moiety of the ester of the benzene carboxylic acid ester in order thus to prevent or significantly retard with certainty any possible re-or transesterification.

Amalgams of any alkali metals can be used as the alkali metal amalgam, preferably sodium amalgam. It is especially desirable to use the kind that is produced in chlorine alkali electrolysis. Preferably, the sodium amalgam used according to the invention has a sodium content between about 0.1 and 0.5%.

The hydrogenation temperatures can be between about 20° and 200° C, preferably close to the boiling temperature of the reaction mixture.

The following examples are given for purposes of comparison and the examples following will serve to explain the invention, without limiting it.

COMPARISON EXAMPLE A (PRIOR ART)

This base experiment describes a procedure by which terephthalic acid dimethyl ster is hydrogenated with sodium amalgam and methanol as in procedure (a) according to the invention, but in the absence of aromatic hydrocarbons.

The reactor is an upright tube made of V4A material and having a length of 2850 mm and an outside diameter of 30 mm. A feed tube having an inside diameter of 8 mm extends into the reactor all the way down to the bottom end, and serves to feed in the reaction solution. Another tube is located at 50 mm from the top edge of the reaction tube for the discharge of the reaction mixture. A valve is fastened to the bottom end of the reaction tube for the removal of the used-up mercury. The reaction tube can be heated by electrical heating wire, and the temperatures are continuously recorded on temperature recorders connected to resistance thermometers. The sodium amalgam serving for the hydrogenation was taken by a chlorine-alkali electrolysis. Depending on the operating conditions, the sodium content of the sodium amalgam varied between about 0.1 and 0.5% sodium in the individual experiments. Before use, the sodium amalgam was shaken with water to remove residues of electrode carbon, and then dried by repeated shaking with absolute methanol. Then the sodium content of the sodium amalgam was determined, and it amounted to 0.38% sodium.

12.0 kg of this sodium amalgam was placed in the reaction tube. Then 76.0 g of terephthalic acid dimethyl ester was dissolved in two liters of methanol, and this solution was warmed in a supply tank to 65° C. This solution was then pumped at a rate of 1.7 liters per hour through the reaction tube, while maintaining a temperature of 65° C. The reaction mixture leaving the reactor was collected in a glass flask. Then pure methanol was pumped through the reactor for a few minutes to flush out the lines. Then the use-up sodium amalgam was let out through the valve at the foot of the reaction tube and the sodium content was determined. The content of sodium in the sodium amalgam diminished during the experiment from 0.38 to 0.12%. During the reaction no molecular hydrogen was released.

The reaction mixture was processed by introducing hydrogen chloride with stirring until a slight excess of acid was present. The sodium chloride that formed was filtered out and the methyl alcohol removed from the filtrate by distillation. The residue was distilled at reduced pressure (at about 1 Torr) and the distillate subjected to a gas-chromatographic analysis in which it was found that the product obtained contains the following components:
p-toluic acid methyl ester — 0.7%
cis-hexahydroterephthalic acid dimethyl ester — 0.6%
trans-hexahydroterephthalic acid dimethyl ester — 0.6%
$\Delta 1$-tetrahydroterephthalic acid dimethyl ester — 55.7%
Terephthalic acid dimethyl ester — 17.2%
p-hydroxymethylbenzoic acid methyl ester — 25.2%.

The yield of $\Delta^1$-tetrahydroterephthalic acid dimethyl ester amunted to 47% of the quantity of reacted terephthalic acid dimethyl ester, while a large part of the product obtained consisted of the undesired p-hydroxymethylbenzoic acid methyl ester.

The $\Delta^1$-tetrahydroterphthalic acid dimethyl ester recrystallizes from hot water in long needles which, after thorough drying, above a melting point of 32.5° C.

EXAMPLE 1

This example illustrates procedure (a) according to the invention.

For the performance of this experiment, the procedure described in the above base experiment is followed, except that a mixture of 0.32 liter of methanol and 1.6 liter of toluene is used instead of methanol alone to dissolve the 76 g of terephthalic acid dimethyl ester.

This hydrogenation is represented by the following equation:

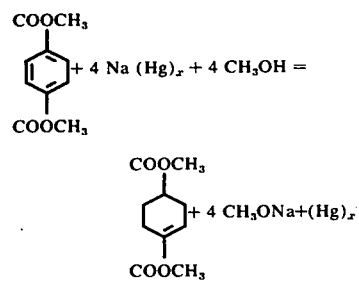

After the sodium chloride is filtered out and the toluene and methanol have been removed by distillation, the residue is distilled at about 1 Torr, the gas chromatography shows that the product obtained contains the following components:
p-toluic acid methyl ester — 3.4%
cis-hexahydroterephthalic acid dimethyl ester — 1.1%
trans-hexahydroterephthalic acid dimethyl ester — 2.2%
$\Delta^1$-tetrahydroterephthalic acid dimethyl ester — 88.7%
terephthalic acid dimethyl ester — 3.7%
p-hydroxymethylbenzoic acid methyl ester — 0.2%.

The yield of $\Delta^1$-tetrahydroterephthalic acid dimethyl ester amounts to 79% of the reacted terephthalic acid dimethyl ester. The yield of undesired p-hydroxymethylbenzoic acid methyl ester amounts to only a fraction of the amount that was formed in the base experiment.

The following Examples 2 and 3 show that, even without the addition of aromatic hydrocarbons the cyclohexenepolycarboxylic acid esters are obtained in a substantially uniform degree of hydrogenation and in a uniform position-isomeric configuration if benzenepolycarboxylic acid esters having ester groups of more than one carbon atom together with alcohols having more than one carbon atom are subjected to hydrogenation with alkali amalgam.

EXAMPLE 2

120 g of terephthalic acid di-n-butyl ester is dissolved in 4 liters of n-butanol, and the solution is poured into a glass flask. At a bath temperature of 87° C, 26 kg of sodium amalga having a sodium content of 0.34% are added drop by drop over a 2 hour period, with stirring and under reflux conditions. No molecular hydrogen evolves. After the end of the experiment the amalgam still had a sodium content of 0.21%. After cooling, the amalgam is separated from the reaction mixture and the reaction solution is neutralized with hydrogen chloride gas. The sodium chloride that formed is removed by centrifugation and the n-butanol is removed by distillation. The residue is distilled in vacuo and a mixture of the hydrogenated terephthalic acid di-n-butyl ester is obtained. The mixture was saponified to identify the composition, and the acids that developed were transformed with methanol to the corresponding methyl esters, since all of the methyl esters of the hydrogenated terephthalic acids are chromatographically known.

The ester mixture then consisted of:
p-toluic acid methyl ester — 2.6%
trans-hexahydroterephthalic acid dimethyl ester — 2.0%
$\Delta^1$-tetrahydroterephthalic acid dimethyl ester — 64.9%
terephthalic acid dimethyl ester — 18.7%
p-hydroxybutylbenzoic acid methyl ester — 0.9%.

EXAMPLE 3

84 g of terephthalic acid diisopropyl ester is dissolved in 1.8 liters of isopropanol; the solution is poured into a glass flask and then, with stirring and under reflux conditions, 13.4 kg of sodium amalgam having a content of 0.33% sodium is added drop by drop during 3 hours. No molecular hydrogen is developed. After the end of the hydrogenation, the amalgam still has a sodium content of 0.12%. After the reaction mixture is cooled, the reaction solution is separated from the amalgam and the reaction solution is neutralized with hydrogen chloride gas. The sodium chloride is removed by centrifuging and the isopropanol is by distillation. The residue is distilled in vacuo, the distillate is saponified, and the acids obtained are esterified with methanol (for analytical reasons).

The mixture consisted of:
p-toluic acid methyl ester — 0.6%
cis- and trans-hexahydroterephthalic acid dimethyl ester — 3.0%
$\Delta^1$-tetrahydroterephthalic acid dimethyl ester — 87.0%
terephthalic acid dimethyl ester — 6.2%

All percentages stated are percentages by weight.

EXAMPLE 4

In a glass flask 20 kg sodium amalgam having a sodium content of 0.30% are covered with a layer of 720 ml benzene. At a reaction temperature of 25° C a mixture of 96 g phthalic acid dimethyl ester and 480 ml methanol was allowed to flow in while stirring. At a sodium content of the amalgam of 0.09% the reaction was completed. The amalgam was separated from the reaction mixture, the reaction solution is acidified with hydrogen chloride gas while stirring and cooling the flask from outside. The sodium chloride produced was filtered off and the solvents distilled off at normal pressure.

The residual hydrophthalic acid esters were subsequently distilled at a pressure of 0.05 Torr in a boiling range of 71° – 90° C. The conversion of the starting product amounted to 90%.

According to gas chromatographic analyses $\Delta^2$-tetrahydro-phthalic acid dimethyl ester and $\Delta^4$-tetrahydrophthalic acid dimethyl ester were obtained at a ratio of 81.5 to 18.5 parts by wt.

EXAMPLE 5

Example 4 is repeated, 90 g isophthalic acid monomethyl ester being used in lieu of the phthalic acid dimethyl ester and 34 kg potassium amalgam having a potassium content of 0.30% in lieu of the sodium amalgam.

A yield of 87% of tetrahydroisophthalic acid dimethyl ester was achieved.

What is claimed is:

1. A process for hydrogenating a diesterified benzene dicarboxylic acid which comprises contacting an alkali metal amalgam, a benzene dicarboxylic acid ester having at least 2 carbon atoms in the ester group and an alcohol having at least 2 and up to 18 carbon atoms at a temperature of about 20° to 200° C.

2. A process according to claim 1 wherein the alkali metal is sodium.

3. A process according to claim 1 wherein the alcohol is the same as the corresponding alcohol of the ester moiety.

4. A process according to claim 1 wherein the process is carried out in the presence of an aromatic hydrocarbon selected from the group consisting of benzene, toluene and xylene.

5. A process according to claim 2 wherein the sodium content of the amalgam is about 0.1 to 0.5 weight percent.

6. A process according to claim 1 wherein said benzene dicarboxylic acid ester is an ester of terephthalic acid.

7. Process for hydrogenating a diesterified benzene dicarboxylic acid which comprises admixing said benzene dicarboxylic acid ester with an alkali metal amalgam, and normal butanol and an aromatic hydrocarbon a substantially anhydrous liquid system; reducing said admixture together at about 20° to 200° C.

8. Process for hydrogenating a diesterified benzene dicarboxylic acid which comprises admixing said benzene dicarboxylic acid ester wth an alkali metal amalgam, and an alcohol having 1 to 18 carbon atoms and toluene in a substantially anhydrous liquid system; reacting said admixture together at about 20° to 200° C.

9. Process for hydrogenating a diesterified benzene dicarboxylic acid which comprises admixing said benzene dicarboxylic acid ester with an alkali metal amalgam, and an alcohol having 1 to 18 carbon atoms and xylene in a substantially anhydrous liquid system; reacting said admixture together at about 20° to 200° C.

10. Process for hydrogenating a diesterified benzene dicarboxylic acid which comprises admixing said benzene dicarboxylic acid ester with a potassium amalgam, and an alcohol having 1 to 18 carbon atoms and an aromatic hydrocarbon with a substantially anhydrous liquid system; reacting said admixture together at about 20° to 200° C.

11. Process for hydrogenating a diesterified benzene dicarboxylic acid which comprises admixing said benzene dicarboxylic acid ester with an alkali metal amalgam, methanol and an aromatic hydrocarbon in a substantially anhyrous liquid system; reducing said admixture together at about 20° to 200° C.

12. Process for hydrogenating a diesterified benzene dicarboxylic acid which comprises admixing said benzene dicarboxylic acid ester with an alkali metal amalgam, and isopropanol; reacting said admixture together at about 20° to 200° C.

13. Process according to claim 12 wherein the reaction mixture contains an aromatic hydrocarbon selected from the group consisting of toluene, benzene and xylene.

* * * * *

UNITED STATES PATENT AND TRADEMARK OFFICE
CERTIFICATE OF CORRECTION

PATENT NO. : 4,024,173
DATED : May 17, 1977
INVENTOR(S) : Arnold Lenz, et al.

It is certified that error appears in the above-identified patent and that said Letters Patent are hereby corrected as shown below:

Column 1, line 43, change "cyclohexane" to --cyclohexene--.

Column 2, line 42, change "ster" to --ester--.

Column 4, line 30, change "amalga" to --amalgam--.

Column 6, line 22, change "wth" to --with--;

line 43, change "anhyrous" to --anhydrous--.

Signed and Sealed this ninth Day of August 1977

[SEAL]

Attest:

RUTH C. MASON
*Attesting Officer*

C. MARSHALL DANN
*Commissioner of Patents and Trademarks*